(12) United States Patent
Roselli et al.

(10) Patent No.: US 6,716,827 B1
(45) Date of Patent: Apr. 6, 2004

(54) COMPLEXES FOR IMMOBILIZING ISOTHIOCYANATE NATURAL PRECURSORS IN CYCLODEXTRINS, PREPARATION AND USE

(75) Inventors: Cécile Roselli, Chaville (FR); Bruno Perly, Le Mesnil Saint Denis (FR); Patrick Rollin, Orleans (FR)

(73) Assignee: Commissariat a l'Energie Atomique, Paris (FR)

(*) Notice: Subject to any disclaimer, the term of this patent is extended or adjusted under 35 U.S.C. 154(b) by 0 days.

(21) Appl. No.: 09/646,792
(22) PCT Filed: Mar. 29, 1999
(86) PCT No.: PCT/FR99/00720
§ 371 (c)(1),
(2), (4) Date: Oct. 17, 2000
(87) PCT Pub. No.: WO99/50307
PCT Pub. Date: Oct. 7, 1999

(30) Foreign Application Priority Data

Mar. 31, 1998 (FR) ............................................. 98 03961

(51) Int. Cl.$^7$ ....................... A61K 31/715; A01N 43/04
(52) U.S. Cl. ............................................ 514/58; 435/18
(58) Field of Search ............................... 514/58; 435/18

(56) References Cited

U.S. PATENT DOCUMENTS

| | | | | |
|---|---|---|---|---|
| 4,528,271 A | * | 7/1985 | Pechany et al. | |
| 4,675,395 A | * | 6/1987 | Fukazawa et al. | ........... 536/103 |
| 5,453,420 A | * | 9/1995 | Sakai | ........................... 514/12 |

FOREIGN PATENT DOCUMENTS

| | | | |
|---|---|---|---|
| EP | 0621287 A | * | 10/1994 |
| JP | 56137867 A2 | * | 10/1981 |
| JP | 402195864 A | * | 8/1990 |
| JP | 05176733 A2 | * | 7/1993 |
| JP | 06158002 A | * | 6/1994 |
| JP | 08245302 A | * | 9/1996 |

OTHER PUBLICATIONS

Taniguchi et al, "Effective Utilization of Horseradich and Wasabi by Treatment with Supercritical Carbon Dioxide", J. Ferment. Technol., (1988) vol. 66, No. 3, pp. 347–353.*

Hanley et al, "Enzymic Hydrolysis of Glucosinolates in a Low Water System", J. Sci. Food Agric. (1990), vol. 51, No. 3, pp. 417–420.*

P. J. Delaquis, et al., Food Technology, pp. 73 to 84, "Antimicrobial Properties of Isothiocyanates in Food Preservation", Nov. 1995.

C. Vaution,et al, Editions de Santé, pp. 299 to 326, "The Use of Cyclodextrins in Various Industries", 1987.

* cited by examiner

Primary Examiner—James O. Wilson
Assistant Examiner—Everett White
(74) Attorney, Agent, or Firm—Oblon, Spivak, McClelland, Maier & Neustadt, P.C.

(57) ABSTRACT

The invention concerns inclusion complexes of precursors from a natural source of organic isothiocyanates, in particular having bacteriostatic, bactericidal and/or fungicidal properties, in cyclodextrins.

The isothiocyanate may meet the formula:

$$R^1-N=C=S \qquad (I)$$

in which $R^1$ is for example the benzyl group. The precursor is a glucosinolate for example.

The complex formed from a precursor may be converted into a complex of the corresponding isothiocyanate through enzymatic hydrolysis with myrosinase.

24 Claims, 3 Drawing Sheets

COMPLEXES FOR IMMOBILIZING ISOTHIOCYANATE NATURAL PRECURSORS IN CYCLODEXTRINS, PREPARATION AND USE

TECHNICAL FIELD

The subject of the present invention is complexes formed by the inclusion of precursors, from a natural source, of organic isothiocyanates in cyclodextrins.

It particularly concerns the solubilisation and/or controlled release of bacteriostatic, bactericidal and/or fungicidal agents formed of organic isothiocyanates, from such complexes.

It also concerns bacteriostatic, bactericidal and/or fungicidal compositions containing such complexes, which can be used in the fields of food and food processing.

STATE OF PRIOR ART

Organic isothiocyantes are known to have remarkable bacterio- and fungistatic properties, and their activity in controlling the proliferation of aerobic and anaerobic microorganisms has been well identified, as described in "Antimicrobial Properties of Isothiocyanates in Food Preservation" by P. J. Delaquis and G. Mazza, published by James Giese in "Food technology", November 1995, pages 73 to 84 [1].

However, their physical properties (they are most often volatile liquids) make their use very difficult in food and food processing applications since it is impossible to control the minimal doses which ensure the preservation process without harming the organoleptic properties of the food to be preserved.

DISCLOSURE OF THE INVENTION

The precise subject of this present invention is bacteriostatic, bactericidal and/or fungicidal compositions in which the organic isothiocyanate is stabilised in the form of an inclusion complex in a cyclodextrin, permitting its solubilisation in an aqueous medium and control over its release.

According to the invention, the inclusion complex is formed of a natural precursor of an organic isothiocyanate included in a cyclodextrin.

According to the invention, the organic isothiocyanate preferably meets the formula:

$$R^1\text{---}N\text{=}C\text{=}S \tag{I}$$

in which $R^1$ represents an alkyl group, whether linear or branched, with 1 to 6 carbon atoms; an alkenyl group, linear or branched, with 2 to 6 carbon atoms; an arylalkyl group in which the alkyl group has 1 to 6 carbon atoms; a group having the formula:

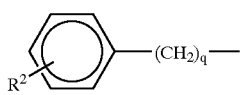

in which q=1 or 2 and $R^2$ represents a hydrogen atom or an alkyl or alkoxyl group with 1 to 3 carbon atoms, the substituent $R^2$ being in ortho, para or meta position; a group with the formula $R^3CO(CH_2)_n$— in which $R^3$ is an alkyl group with 1 to 3 carbon atoms and n is a whole number of 3 or 4; a group with the formula $R^3OCO(CH_2)_n$— in which $R^3$ and n are as defined above; a methylthioalkyl group with the formula $CH_3S(CH_2)_p$— in which p is a whole number from 1 to 10; or a group with the formula $CH_3$—S—CH=CH—$(CH_2)_r$— in which r is a whole number from 1 to 8.

As an example of such isothiocyanates, mention may be made of those for which $R^1$ has the denotation given in the appended table.

The natural precursor of organic isothiocyanate, or glucosinolate, may meet the formula:

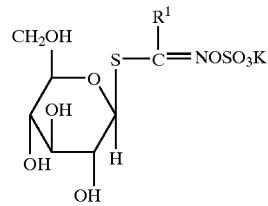

(IV)

in which $R^1$ has the denotation given above.

These natural precursors may in particular be those mentioned in the appended table.

These natural precursors may be obtained from plant sources such as those also listed in the appended table.

The cyclodextrin used in the inclusion complex described above may be a natural cyclodextrin or a chemically modified cyclodextrin.

It is recalled that the cyclodextrins or cyclomaltooligosaccharides are compounds of natural origin, formed by the chain conformation of glucose units bonded at α-1.4.

The natural cyclodextrins are α-cyclodextrin which contains 6 glucose units, β-cyclodextrin which contains 7 glucose units and γ-cyclodextrin which contains 8 glucose units. Much research work has shown that these cyclodextrins could form inclusion complexes with hydrophobic molecules, thereby permitting their solubilisation in aqueous media and their use in various industries, as described in the work entitled: "Cyclodextrins and their Industrial Uses" by D. Duchêne published by Editions de Santé, 1987, pages 299 to 326, [2].

According to the invention, not only a natural cyclodextrin may be used, but also a natural cyclodextrin that is chemically modified through the addition of appropriate substituents. Said modified cyclodextrin may meet the formula:

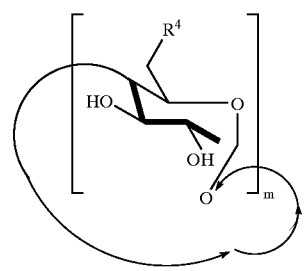

(II)

in which m=6, 7 or 8 and the $R^4$s which may be identical or different, represent OH or a group chosen from among the X-alkylated or X-arylated groups in which X represents a carbon atom or a heteroatom provided that at least one of the $R^4$s is not OH.

In this case, the substituents $R^4$ of cyclodextrin are chosen such as to improve its properties, in particular in respect of the solubilisation and stabilisation of the organic isothiocyanates.

According to the invention, the inclusion complex of a natural precursor of an organic isothiocycate in a cyclodextrin, using an aqueous solution of cyclodextrin, may be prepared by the addition of the natural precursor to this solution. The cyclodextrins used are those previously described.

In this manner, the inclusion complex may be formed either in the form of an aqueous solution, or in the form of a precipitate which is subsequently separated from the solution. In this latter case, an aqueous solution saturated with cyclodextrin may be used.

According to the invention, the inclusion complexes of natural precursors of organic isothiocyanates in cyclodextrins may be used to prepare an inclusion complex of an organic isothyanate in a cyclodextrin.

Indeed, it is known that these natural precursors of organic isothiocyanates may be converted into the corresponding isothiocyanates by hydrolytic reaction with myrosinase in accordance with the following reaction diagram:

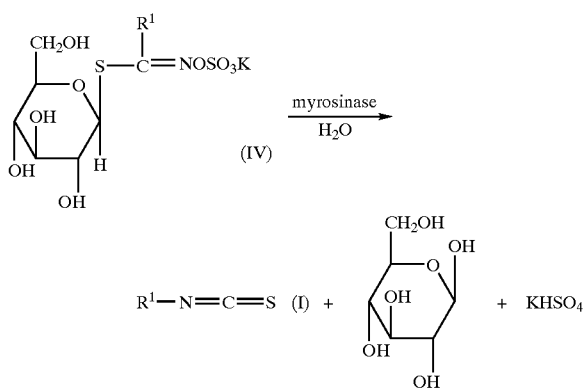

Myrosinase is an enzyme naturally present in Cruciferae. The enzymatic hydrolysis of the natural precursor of formula (IV) by myrosinase leads to the corresponding organic isothiocyanate and to the release of a molecule of D-glucose and potassium acid sulphate.

According to the invention, it has been discovered that it is possible to prepare an inclusion complex containing organic isothiocyanate from an inclusion complex containing the natural precursor of this isothiocyanate through the action of myrosinase on this complex.

Therefore, a further object of this invention is a method for preparing an inclusion complex formed of an organic isothiocyanate included in a cyclodextrin, which comprises the following steps:

a) preparing, in an aqueous solution, an inclusion complex containing a natural precursor of an organic isothiocyanate in cyclodextrin, and b) submitting the complex so obtained to the action of myrosinase in aqueous solution to convert the natural precursor included in the cyclodextrin into the corresponding organic isothiocyanate.

In this case, the aqueous solution used in the second step, and optionally in the first step, is a solution suitable for hydrolysis by myrosinase. It may be a buffer solution such as a phosphate buffer solution with a pH value of 6.

A further object of the invention is a bacteriostatic, bactericidal and/or fungicidal composition, made up of a dry mixture containing:

a) an inclusion complex of a natural precursor of an organic isothiocyanate, having bactericidal, bacteriostatic and/or fungicidial properties, in a cyclodextrin, and b) myrosinase.

By way of example, the composition may be in powder, granule, wettable powder form etc. This composition may comprise appropriate vehicles and additives such as those generally used for the production of bacteriostatic, bactericidal and/or fungicidal products intended for the food or food processing industries.

It may be prepared using conventional methods.

With this composition, at the time of use, when the dry mixture is placed in contact with water or a humid atmosphere, the presence of water will convert the natural precursor present in the inclusion complex into the corresponding organic isothiocyanate through enzymatic hydrolysis with the myrosinase in the composition.

In this case, the composition is for example in powder form, or wettable powder form.

Other characteristics and advantages of the invention will be better understood on reading the following description of embodiments given evidently for illustrative, non-restrictive purposes with reference to the appended drawings.

SHORT DESCRIPTION OF THE DRAWINGS

DETAILED DESCRIPTION OF EMBODIMENTS

The following examples illustrate the preparation of complexes in accordance with the invention using the natural precursor of benzyl isothiocyanate (benzyl-ITC) which is the glucosinolate derived from Tropaeolum Majus.

The benzyl isothiocyanate meets the formula (III) below:

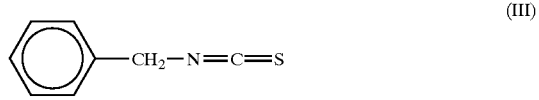

(III)

This compound is in the form of an oily liquid, insoluble in water, which is very delicate to handle on account of its properties and volatility.

EXAMPLE 1

Preparation of an Inclusion Complex of the Glucosinolate Precursor of Benzyl Isothiocyanate in α-Cyclodextrin In this example, a solution is prepared containing 2.2 mg α-cyclodextrin in 400 μl of 50 mM deuterated phosphate buffer, pH=6, to which is added 7.5 mg of the glucosinolate precursor of benzyl ITC derived from Tropaeolum Majus or glucotropaeoline. This precursor meets the formula:

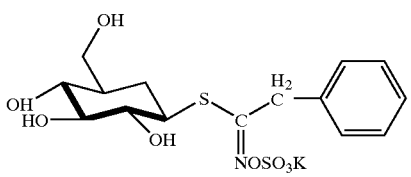

(V)

The formation of this complex is checked by recording the NMR spectrum at 25° C. and 500 MHz of the solution before and after the addition of the glucosinolate.

Figure 1:
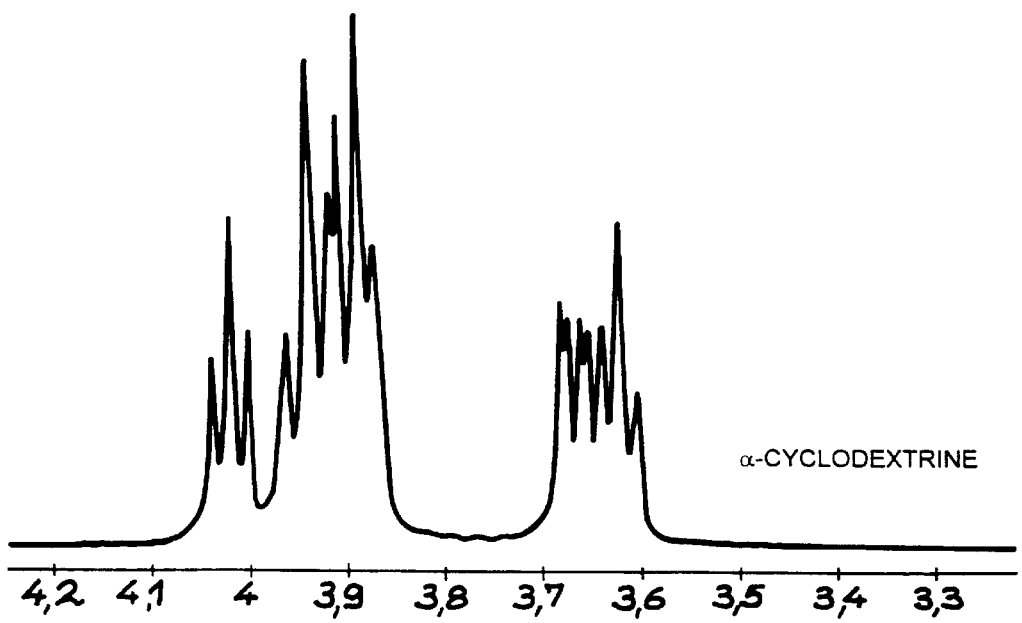
FIG. 1 is the partial nuclear magnetic resonance spectrum of 10 mM α-cyclodextrin in $D_2O$ at 25° C., recorded at 500 MHz.

FIG. 1 shows the spectrum of the α-cyclodextrin solution before addition.

Figure 2:
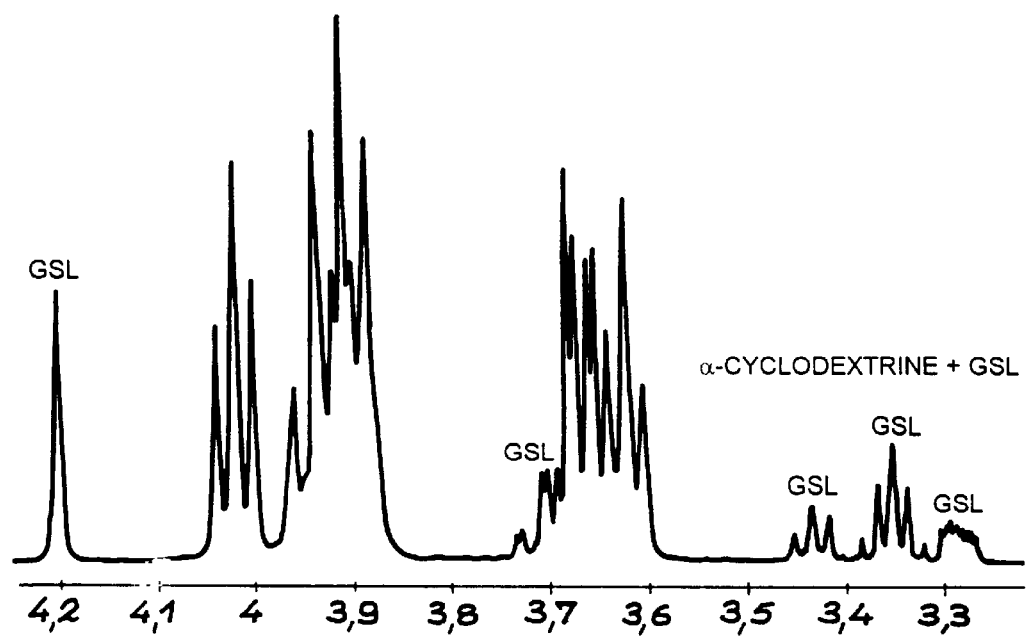
FIG. 2 is the partial NMR spectrum of the α-cyclodextrin-Tropaeolum Majus glucosinolate complex in $D_2O$ at 25° C., recorded at 500 MHz.

FIG. 2 shows the NMR spectrum taken under the same conditions, after addition of the glucosinolate (GSL).

This leads to the observation of signals corresponding to the glucosinolate (GSL) at 4.2, 3.7, 3.4, 3.35 and 3.28 ppm.

Figure 3:
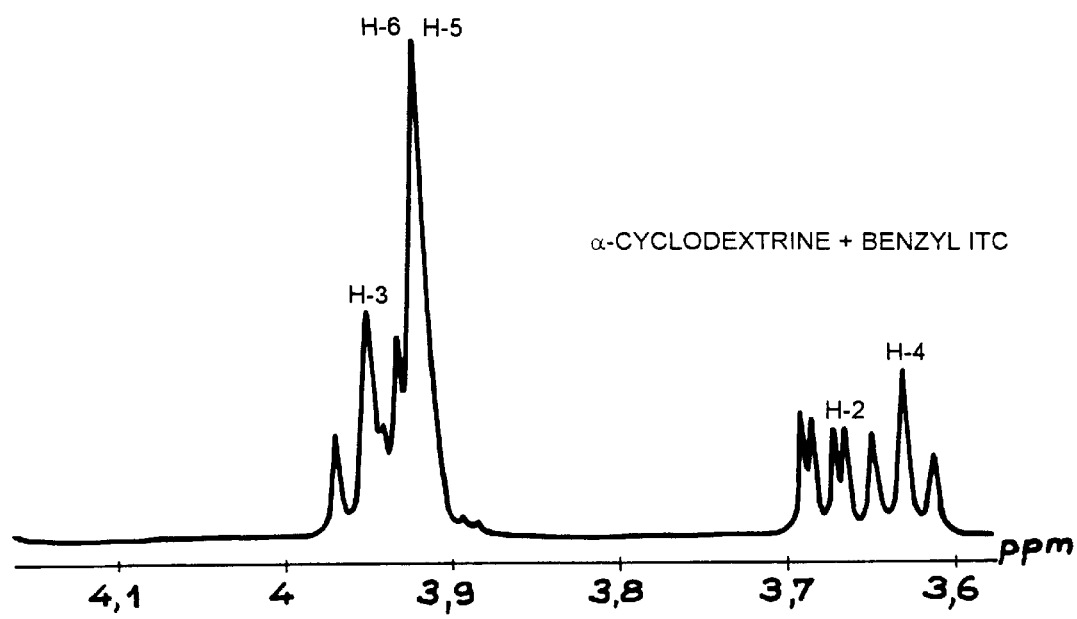
FIG. 3 is the partial NMR spectrum of the α-cyclodextrin-benzyl ITC complex in $D_2O$ at 25° C., recorded at 500 MHz.

By way of comparison, FIG. 3 shows the NMR spectrum obtained at 25° C. and 500 MHz of the inclusion complex of benzyl isothiocyanate (benzyl-ITC) in α-cyclodextrin obtained in the following manner.

2.2 mg of α-cyclodextrin are dissolved in 400 μl of $D_2O$. To this solution 0.3 μl of benzyl isothiocyanate (benzyl-ITC) are added and in this manner the inclusion complex of this isothiocyanate in α-cyclodextrin is obtained.

Figure 6:
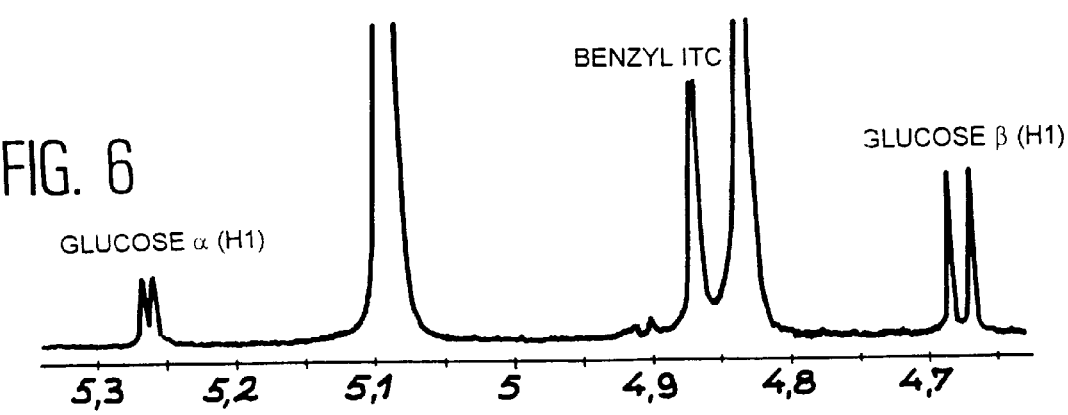

FIG. 6 shows the NMR spectrum obtained after the addition of benzyl isothiocyanate.

A comparison of this spectrum with that of FIG. 1 shows the formation of an inclusion complex, in particular by the displacement of the H-3 and H-5 signals of cyclodextrin positioned inside the cavity. The use of bidimensional NMR methods can provide a structure model of this complex in which the benzyl part of the benzyl-ITC is inside the cavity of the cyclodextrin.

EXAMPLE 2

In this example, the inclusion complex formed in example 1 is converted into an inclusion complex of benzyl isothiocyanate in the cyclodextrin.

For this purpose, myrosinase is added to the solution of the complex prepared in example 1, then hydrolysis of the glucosinolate is followed under nuclear magnetic resonance.

Figure 4:
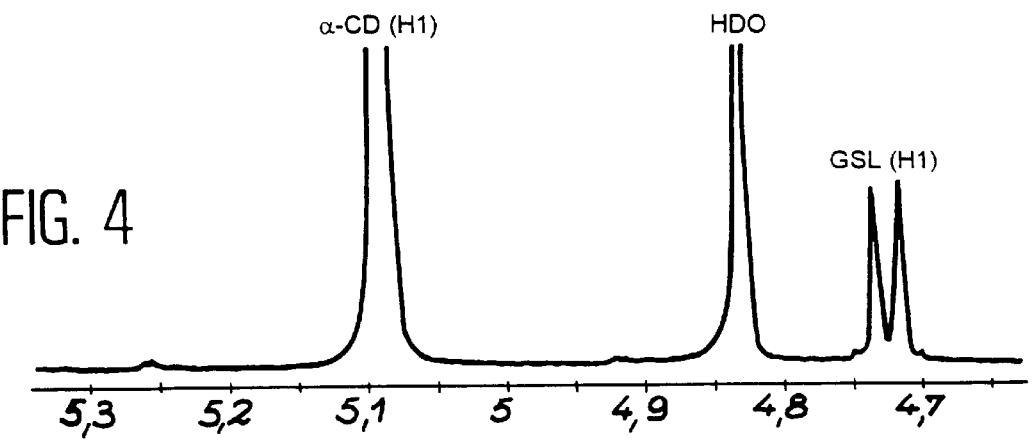
FIGS. 4 to 6 are partial NMR spectra of the α-cyclodextrin-Tropaeolum Majus glucosinolate complex in the presence of myrosinase at 25° C., recorded at 500 MHz, before the addition of myrosinase (FIG. 4), 1 h after this addition (FIG. 5) and 17 h after this addition (FIG. 6).
Figure 5:
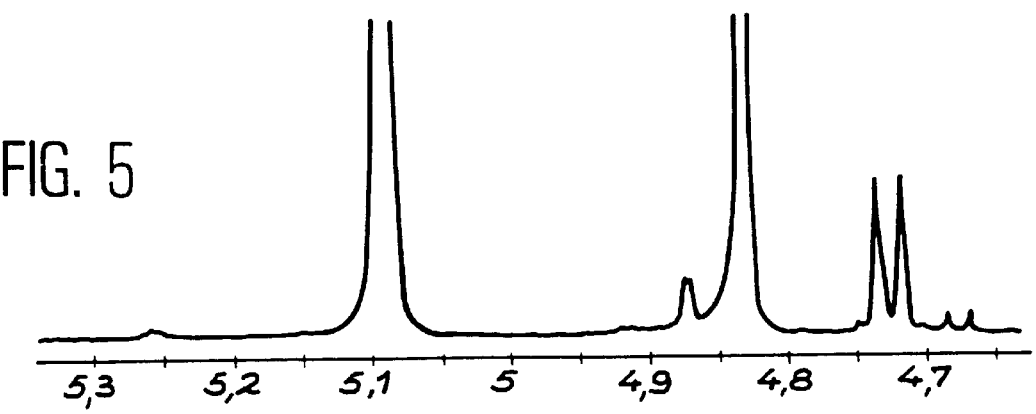

The results are given in FIGS. 4, 5 and 6 which illustrate the NMR spectra obtained at 25° C. and 500 MHz, before the addition of myrosinase (FIG. 4), 1 hour after the addition of myrosinase (FIG. 5), and 17 hours after the addition of myrosinase (FIG. 6).

If these spectra are compared, it is observed that the spectrum in FIG. 6 contains signals corresponding to α-glucose, to β-glucose and to benzyl isothiocyanate, which signals do not exist in FIG. 4 and which start to form in FIG. 5.

Also, it is noted that the benzyl isothiocyanate formed by the action of myrosinase is always complexed in the cyclodextrin and therefore remains soluble in an aqueous solution.

Cited References

[1]: "Antimicrobial Properties of Isothiocyanates in Food Preservation" by P. J. Delaquis and G. Mazza, published by James Giese in "Food technology", November 1995, pages 73 to 84.

[2]: "Cyclodextrins and their Industrial Uses", by D. Duchêne, published by Editions de Santé, 1987, pages 299 to 326.

TABLE 1

| Isothiocyanates $R^1$—N═C═S | Precursor | Plant sources |
|---|---|---|
| $R^1$ | GSL | |
| methyl | Glucoapparin | Boscia senegalensis |
| ethyl | Glucolepidin | |
| propyl | | |
| isopropyl | Glucopurtanjivin | Sysymbrium officinale (sisymbre) |
| n-butyl | | |
| isobutyl | | |
| s-butyl | Glucocochlearin | |
| 3-methylbutyl | | |
| 2-methylbutyl | Glucojiaputin | |
| allyl | Sinigrin (SIN) | Brassica nigra (black mustard) |
| but-3-enyl | Gluconapin (GNA) | isatis tinctoria (pastel) |
| pent-4-enyl | Glucobrassicanapin (GBN) | |
| benzyl | Glucotropaeolin (GTL) | Tropaeolum majus (nasturtium) |
| 2-phenylethyl | Gluconasturtin (GST) | Nasturtium officinale (watercress) |
| p-methoxybenzyl | Glucoaubrietin | Aubrietia sp. |
| m-methoxybenzyl | Glucolimnanthin GSL | |
| p-hydroxybenzyl | Glucosinalbine | Sinapis alba/arvensis (white/wild mustard) |
| 1) $EtCO(CH_2)_4$ | Gluconorcappasalin | |
| 2) $PrCO(CH_2)_4$ | Glucocappasalin | |
| $PrCO\ (CH_2)_3$ | Glucocapangulin | |
| $EtOCO\ (CH_2)_3$ | Glucoerypestrin | |
| 3) $MeS(CH_2)_3$ | Glucoibervirin (GIV) | |
| $MeS(CH_2)_4$ | Glucoerucin (GER) | Eruca sativa (sweet rocket) |
| $MeSCH═CH(CH_2)_2$ | Glucoraphasatin | Raphanus sativus (radish) |
| $MeS(CH_2)_5$ | Glucoberteroin | |
| $MeS(CH_2)_6$ | Glucolesquerellin | Lesquerella sp. |
| $MeS(CH_2)_8$ | Glucojirsutin | Arabis sp. |
| $MeS(CH_2)_9$ | Glucoarabin | Arabis sp. |

1) Et = ethyl
2) Pr = propyl
3) Me = methyl

What is claimed is:

1. A composition comprising:

an inclusion complex of a natural precursor of an organic isothiocyanate and a cyclodextrin, said natural precursor of the organic isothiocyanate being convertible into the corresponding organic isothiocyanate by a myrosinase, and a myrosinase;

wherein said composition is in a dry form, and wherein the cyclodextrin comprises the following formula:

(II)

in which m=6, 7 or 8 and the $R^4$ groups, which may be identical or different, represent OH or an X-alkylated or X-arylated group in which X represents a carbon atom or a heteroatom, provided that at least one of the $R^4$ group(s) is not OH.

2. The composition of claim 1, wherein said natural precursor is a precursor of an organic isothiocyanate having the following formula:

$R^1$—N=C=S     (I), wherein $R^1$ is an alkyl group, linear or branched, with 1 to 6 carbon atom(s).

3. The composition of claim 1, wherein said natural precursor is a precursor of an organic isothiocyanate having the following formula:

$R^1$—N=C=S     (I), wherein $R^1$ is an alkenyl group, linear or branched, with 2 to 6 carbon atoms.

4. The composition of claim 1, wherein said natural precursor is a precursor of an organic isothiocyanate having the following formula:

$R^1$—N=C=S     (I), wherein $R^1$ is an alkyl group.

5. The composition of claim 1, wherein said natural precursor is a precursor of an organic isothiocyanate having the following formula:

$R^1$—N=C=S     (I), wherein $R^1$ is an arylalkyl group in which the alkyl group has 1 to 6 carbon atom(s).

6. The composition of claim 1, wherein said natural precursor is a precursor of an organic isothiocyanate having the following formula:

$R^1$—N=C=S     (I), wherein $R^1$ is a group with the formula:

$R^2$—⟨phenyl⟩—$(CH_3)_q$— in which q=1 or 2 and $R^2$ represents a hydrogen atom or an alkyl or alkoxyl group with 1 to 3 carbon atoms, the substituent $R^2$ being in the ortho, para or meta position.

7. The composition of claim 1, wherein the natural precursor of an organic isothiocyanate comprises the following formula:

(IV)

in which $R^1$ represents an alkyl group, linear or branched, with 1 to 6 carbon atom(s); an alkenyl group, linear or branched, with 2 to 6 carbon atoms; an arylalkyl group in which the alkyl group has 1 to 6 carbon atom(s); a group with the formula:

$R^2$—⟨phenyl⟩—$(CH_3)_q$— in which q=1 or 2 and $R^2$ represents a hydrogen atom or an alkyl or alkoxyl group with 1 to 3 carbon atoms, the substituent $R^2$ being in ortho, paxa or meta position; a group with the formula $R^3CO(CH_2)_n$— in which $R^3$ is an alkyl group with 1 to 3 carbon atom(s) and n is a whole number of 3 or 4; a group with the formula $R^3OCO(CH_2)_n$— in which $R^3$ and n are as defined above; a methylthioalkyl group with the formula $CH_3S(CH_2)_p$— in which p is a whole number from 1 to 10; or a group with the formula $CH_3$—S—CH=CH—$(CH_2)_r$— in which r is a whole number from 1 to 8.

8. The composition of claim 1, wherein the natural precursor of an organic isothiocyanate selected from the group consisting of glucoapparin, glucolepidin, glucoputranjivin, glucocochlearin, glucojiaputin, sinigrin, glucoapin, glucobrassicanapin, glucotropaeolin, gluconasturtin, glucoaibrietin, glucolimnanthin, glucosinalbin, gluconorcappasalin, glucocappasalin, glucocapangulin, glucoerypestrin, glucoibervirin, glucoerucin, glucoraphasatin, glucoberteroin, glucolesquerellin, glucohirsutin and glucoarabin.

9. The composition of claim 1, wherein the natural precursor of an organic isothiocyanate is glucotropaeolin and the cyclodextrin is α-cyclodextrin.

10. The composition of claim 1 in the form of a powder.

11. The composition of claim 1 that is a wettable powder.

12. The composition of claim 1 in the form of a granule.

13. The composition of claim 1, wherein said natural precursor is a precursor of an organic isothiocyanate having the following formula:

$R^1$—N=C=S     (I), wherein $R^1$ is a group with the formula $R^3CO(CH_2)_n$— in which $R^3$ is an alkyl group with 1 to 3 carbon atom(s) and n is a whole number of 3 or 4.

14. The composition of claim 1, wherein said natural precursor is a precursor of an organic isothiocyanate having the following formula:

$R^1$—N=C=S     (I), wherein $R^1$ is a group with the formula $R^3OCO(CH_2)_n$— in which $R^3$ is an alkyl group with 1 to 3 carbon atom(s) and n is a whole number of 3 or 4.

15. The composition of claim 1, wherein said natural precursor is a precursor of an organic isothiocyanate having the following formula:

$$R^1\!-\!N\!=\!C\!=\!S \qquad (I),$$

wherein $R^1$ is a methylthioalkyl group with the formula $CH_3S(CH_2)_p\!-\!$ in which p is a whole number from 1 to 10.

16. The composition of claim 1, wherein said natural precursor is a precursor of an organic isothiocyanate having the following formula:

$$R^1\!-\!N\!=\!C\!=\!S \qquad (I),$$

wherein $R^1$ is a group with the formula $CH_3\!-\!S\!-\!CH\!=\!CH\!-\!(CH_2)_r\!-\!$ in which r is a whole number from 1 to 8.

17. The composition of claim 1, wherein the cyclodextrin is an α-cyclodextrin.

18. The composition of claim 1, wherein the cyclodextrin is a β-cyclodextrin.

19. The composition of claim 1, wherein the cyclodextrin is a γ-cyclodextrin.

20. A food to which the composition of claim 1 has been added.

21. An aqueous solution to which the composition of claim 1 has been added.

22. A method for producing a bacteriostatic, bacteriocidal or fungicidal organic isothiocyanate comprising contacting the composition of claim 1 with water.

23. A method for inhibiting the growth of a microorganism comprising contacting the composition of claim 1 with water.

24. A method for inhibiting the growth of a bacterium comprising contacting the composition of claim 1 with water.

* * * * *